United States Patent [19]
Souder

[11] Patent Number: 5,817,000
[45] Date of Patent: Oct. 6, 1998

[54] MAGNETIC THERAPY DEVICE

[76] Inventor: James Souder, 4105 Starboard Ct., Raleigh, N.C. 27613

[21] Appl. No.: 712,108

[22] Filed: Sep. 13, 1996

Related U.S. Application Data

[60] Provisional application No. 60/003,692 Sep. 13, 1995.
[51] Int. Cl.$^6$ ....................................................... A61N 1/00
[52] U.S. Cl. ................................................................ 600/15
[58] Field of Search ............................................ 600/9–15

[56] References Cited

U.S. PATENT DOCUMENTS

| | | |
|---|---|---|
| 749,213 | 1/1904 | Muller . |
| 1,164,356 | 12/1915 | Kaiser . |
| 1,624,397 | 4/1927 | Dequer . |
| 3,103,925 | 9/1963 | Vogt . |
| 4,177,796 | 12/1979 | Franco-Vila . |
| 4,401,109 | 8/1983 | Dejong . |
| 4,682,584 | 7/1987 | Pose . |
| 4,691,693 | 9/1987 | Sato . |
| 4,727,857 | 3/1988 | Horl . |
| 4,744,350 | 5/1988 | Sato . |
| 4,850,340 | 7/1989 | Onishi . |
| 5,017,185 | 5/1991 | Baermann et al. . |
| 5,027,795 | 7/1991 | Kato . |
| 5,084,003 | 1/1992 | Susic . |
| 5,092,835 | 3/1992 | Schurig et al. . |
| 5,135,466 | 8/1992 | Fedorov et al. . |
| 5,226,020 | 7/1993 | Li et al. . |
| 5,233,768 | 8/1993 | Humphreys et al. . |
| 5,295,494 | 3/1994 | Rodriguez . |
| 5,323,499 | 6/1994 | Chan . |
| 5,330,410 | 7/1994 | Baylink . |
| 5,382,222 | 1/1995 | Yih-Jong . |
| 5,387,176 | 2/1995 | Markoll . |
| 5,389,981 | 2/1995 | Riach . |
| 5,429,585 | 7/1995 | Liang . |
| 5,437,600 | 8/1995 | Liboff et al. . |
| 5,441,495 | 8/1995 | Liboff et al. . |

Primary Examiner—John P. Lacyk
Attorney, Agent, or Firm—Gifford, Krass, Groh, Sprinkle, Patmore, Anderson & Citkowski

[57] ABSTRACT

The present invention relates to the application of a moving magnetic field whereby a magnet moveable in a horizontal or vertical direction is placed proximate the user. The magnet is preferably contained within the interior cavity of a housing, the interior cavity being larger than the magnet, and the housing being positioned proximate to the user such that, as the magnet moves within the interior cavity of the housing, a moving magnetic field is generated which interacts with the surrounding tissue of the user. The housing may be attached to the user or to an object proximate to the user such that movements of the user or object cause the magnet within the interior cavity of the housing to move with respect to the user. Alternate embodiments include disposing the magnet on the end of a flexible handle or in an array.

23 Claims, 4 Drawing Sheets

Reference Line A

Reference Line B

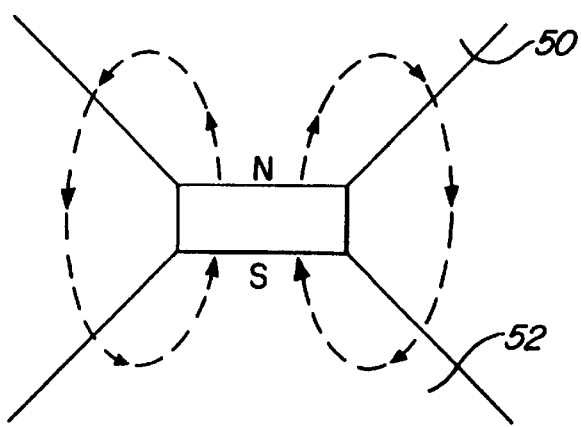
FIG-10 PRIOR ART
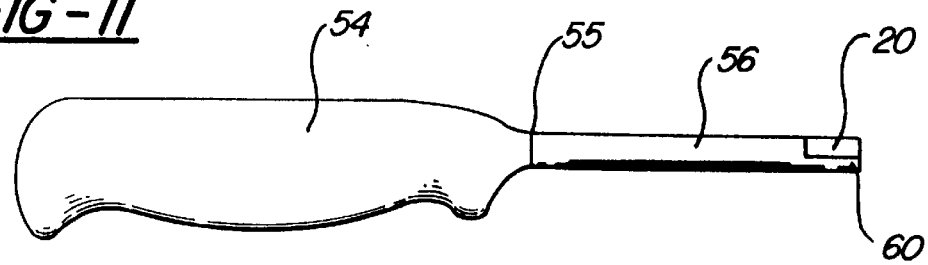
FIG-11
FIG-12
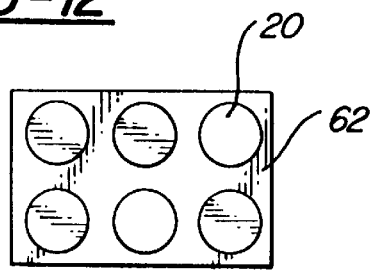
FIG-13
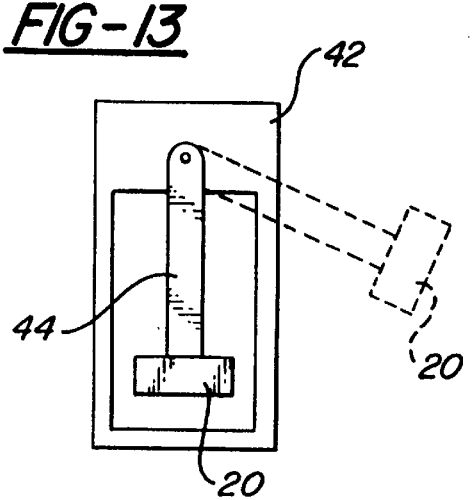

MAGNETIC THERAPY DEVICE

CROSS-REFERENCE TO PRIOR APPLICATION

This application claims the benefit of U.S. Provisional Application 60/003,692 filed Sep. 13, 1995.

FIELD OF THE INVENTION

The present invention relates generally to therapeutic devices, and more particularly to such therapeutic devices which utilize magnetic fields.

BACKGROUND OF THE INVENTION

Magnetic fields have been employed for a variety of therapeutic purposes, including relief of pain and inflammation from soft tissue injury and musculoskeletal injury, relaxation of muscles, relief of headaches, treatment of internal organs and a variety of other therapeutic applications. Additionally, magnetic fields have been utilized to enhance and control the timing of plant growth. Magnetic fields are known to increase circulation and blood flow in the tissues subjected to the magnetic field. Magnetic fields have also proven effective in treatment of arthritis and have also been claimed to dissolve calciferous plaques and deposits in the bodies of humans and animals.

Relative movement between the tissue and magnetic field has been shown to cause increased electron flow (eddy current generation) through the tissue and is also associated with the activation of capillary blood flow and relaxation of muscle. Research has demonstrated the superiority of a dynamic magnetic field having temporally varying magnetic flux density for enhanced activation of capillary blood flow. Microscopic examination of rat mesentery subjected to dynamic magnet fields has shown an increase of capillary activation in response to an oscillating magnetic field developed by oscillation of a permanent magnet in proximity to the subject tissue, whereas no such effect was observed from placement of a static magnet field in the same proximity to such tissue. Beneficial effects have been observed utilizing magnets having field strengths from less than one Hertz to over 500 Hertz with no define cutoff threshold identified in response to increased frequencies. Additionally, relaxation of muscle tissue has been noted when a magnetic field, oscillating at 80 Hertz, interacts with such tissue. Moving magnetic fields are also reported to have a pain-reducing effect on arthritis joint pain.

A further consideration in magnetic therapy devices is the selection of north pole versus south pole fields for therapeutic applications. Numerous books have been published by Albert Davis, William Philpott M.D. and others proclaiming differentiated effects between north and south pole magnetic fields as disclosed in U.S. Pat. No. 5,389,981 to Riach. Although magnetic fields are a continuous phenomena, there are subtle differences between north pole (or divergent) fields, south pole (or convergent) fields and mixed fields containing both divergent and convergent flux patterns. The benefits of enhanced performance of dynamic fields may be achieved while preserving the orientation of polarity toward the individual by employing magnets in arrays that maintain pole orientation toward the individual while incorporating movement. It is frequently desirable to maintain field orientation to deliver specific therapeutic applications with north pole or south pole fields directed at the individual while, at the same time, moving the magnet sources relative to the individual (permanent magnets or DC electromagnets of specified pole orientation). The resulting varying field will produce the intensified response of a dynamic field while maintaining the polar preference of the individual.

It should be noted that the spacing between magnet sources and distance between the magnet and individual will determine if the subject will experience return path flux of the opposite polarity between magnet sources. If a pure field of either pole is required, the magnetic elements can be positioned either closer to each other on a moving array or the array can be moved farther from the subject exactly as would be practiced with a static array to avoid field reversal in the void between discrete magnetic elements.

It is preferable to utilize permanent magnets to provide the magnetic fields as relatively powerful fields can be provided with no energy input required to generate the field. However, special circumstances could confer an advantage on electromagnet sources. DC electromagnets would provide the benefit of maintaining specified pole orientation. The physical movement of an AC electromagnet relative to the individual could effectively increase the kinetic coupling of the device to tissue.

Typical prior applications have placed permanent magnets within devices which are moved over affected target tissues or secured to the user so that the magnet does not move relative to the user.

U.S. Pat. No. 5,226,020 to Li et al. discloses a wristwatch having a magnetic body which is proximate to the skin of the user when the wristwatch is worn. A magnetic isolating piece is disposed between the time-keeping mechanism and the magnetic body so as to prevent the magnetic body from interfering with the operation of the time-keeping piece. Although the wristwatch disclosed by Li et al. incorporates a magnet placed proximate to the skin of the user, the magnetic body remains stationary with respect to the wearer, and does not subject the wearer to a moving magnetic field.

U.S. Pat. No. 5,389,981 to Riach Jr. discloses eyeglasses having magnets attached thereto so as to subject the eyes to magnetic energy. The magnets are positioned on the eyeglasses to project a north magnetic field into the surrounding area of the eyes to improve blood circulation. The device disclosed by Riach Jr. includes stationary magnets and is intended to project a stationary magnetic field over the eyes.

U.S. Pat. No. 5,295,494 to Rodriguez discloses a housing having a magnet securely positioned therein, the housing configured to accept a band to secure the housing to a user. The configuration of the housing prevents movement of the magnet within the interior of the housing. Thus, the wearer is subjected to a stationary rather than a moving magnetic field. The device disclosed by Onishi in U.S. Pat. No. 4,850,340 likewise utilizes hollow cases containing a magnet, each case configured so as to be pivotably linked to other cases. The magnetic field generator contained within each case is fixed in a stationary position within the case. Thus, the wearer of the Onishi device is subjected to a stationary rather than a moving magnetic field.

U.S. Pat. No. 4,177,796 to Franco-Vila discloses a device for the treatment of arthritis which utilizes a pair of magnets, one magnet affixed to each side of an elastic band which is placed across the end of a housing containing an electromagnet. The paired magnets are caused to vibrate by application of a low frequency alternating magnetic field which causes the magnets and the elastic band to vibrate, so that, upon placing the end of the housing next to the injured tissue, vibration of the magnets acts to massage the tissue. The electromagnet subjects the tissue to be treated to a magnetic field, while the vibrating elastic band subjects the tissue to vibration.

U.S. Pat. No. 5,027,795 to Kato et al. discloses a massage machine to be utilized in conjunction with a seat in a vehicle. The device is configured to dispose magnets between the person in the seat and the seat, the magnets being non-moveably affixed to the frame which is positioned on the seat of the vehicle. The magnets of the Kato device are not moved with respect to the user.

U.S. Pat. No. 4,682,584 to Pose discloses a dental care instrument for treating emissions of foreign bodies within the mouth, the instrument having, at its operative end, a magnet which is placed within a patient's mouth. The end of the dental instrument is moved relative to the teeth, thus moving the magnet relative to the teeth. While in some embodiments the magnet is affixed to the end of the dental instrument so that it is rotatable about the end of the dental instrument, alternate embodiments provide a magnet fixed in a stationary position. While the Pose device does provide a relatively simple mechanism for applying a magnetic field to an area to be treated, the user or individual providing treatment must move the dental care instrument with respect to the area to be treated to achieve movement of the magnet.

Likewise, U.S. Pat. No. 4,744,350 to Sato and U.S. Pat. No. 5,382,222 to Yih-Jong both disclose massaging devices having magnets embedded therein, each device being moveable over the area to be treated.

U.S. Pat. No. 5,323,499 to Chan discloses a mattress including a layer of alternating wooden beads and magnets, the magnets providing a static magnetic field on which the user may rest, the alternating magnets and beads applying a massaging action to the user. The mattress magnets apply a stationary magnetic field to the individual as the individual is sleeping upon the mattress.

Permanent magnets may be inertially mounted to the body of an individual so that the movement of the host will create relative movement of the magnet and the target tissue. Permanent or electrical magnets may be used. The inertial mount can be applied to surrounding environments through which the individual moves, such as a truck, desk or stationary support elements of a swing whereby the individual moves through the therapeutic magnetic field.

The inertial mounting system will increase the effectiveness of interaction between individual and the magnetic field by moving the magnetic source relative to the individual. Relative movement between the individual and magnet is provided by the natural movement of the individual, which may additionally cause movement of the magnet. The magnets may be mounted, for example, in the supporting frame of a porch swing so that the swinging motion of the individual in the chair portion of the swing causes relative motion between the magnet and individual.

Such systems provide a changing magnetic field relative to the individual which may help to reduce muscle stiffness and discomfort for persons confined to one position for extended periods such as truck drivers and persons confined to a bed or a chair.

The present invention combines the benefits of portability associated with easily applied permanent magnetic devices with moving magnetic fields relative to tissue. The present invention improves upon prior art biomagnetic devices by providing enhanced relative movement between the magnet and the subject tissue by physically moving the magnetic source. The present invention provides a means for the magnet to be moved relative to the subject tissue in response to inertial or other mechanical energy inputs incidental to the activity of the individual.

SUMMARY OF THE INVENTION

The present invention relates to a therapeutic device for subjecting a user to a moving magnetic field, the therapeutic device including a moveable magnet positioned proximate to a user. The magnet is preferably contained within the interior cavity of a housing, the interior cavity being larger than the magnet so that the magnet is freely moveable within the interior cavity. The housing may be configured so as to assure the polarity of the magnetic field remains the same with respect to a particular side of the housing, thus permitting the user to be exposed to a moving magnetic field having a substantially single polarity. The housing is positioned on or embedded in a user. Alternately, the magnet may be suspended from a frame or other object by elastic members such as springs or elastic bands, or pivotable members and the like so that the magnet may move relative to the frame or object, the frame or object being positioned proximate to the user. Movement of the magnet by inertial or other forces provides a moving magnetic field which interacts with the surrounding tissue of the user.

Although permanent magnets may be used, electromagnets will achieve similar results. A single housing may contain a plurality of magnets, and a plurality of magnets may be used to form an array to produce a pulsing or temporally variable unipolar magnetic field which may be preferred for applications which are deemed best treated with a magnetic field having a specific pole.

Preferably, the housings, frames and arrays are affixed to the user or the user's clothing by adhesive, velcro or other mounting means. The housings, frames and arrays may be placed within shoes such as sneakers, tennis racquets, baseball bats, and the like.

Alternatively, the housings may be positioned on or within a moving object within the individual's environment, such as a seat in a vehicle, a fan such as a ceiling fan, a steering wheel, or the hand wheel of a wheelchair. For example, a housing or a plurality of housings, each containing at least one magnet, may be affixed to the supports of a swing or the swing seat itself, thereby subjecting the user swinging in the seat to a varying magnetic field.

An alternate embodiment of the present invention includes a handle having an end and a permanent or other type of magnet. Disposed between the handle end and magnet is a flexible member so that, as the handle is moved, the movement of the magnet proximate to the user is accentuated, permitting the application of an accentuated moving magnetic field.

Yet another embodiment of the present invention comprises a substantially planar member upon which are affixed a plurality of magnets. Means are provided for moving the substantially planar member substantially parallel to a user. Thus, the magnets may be oriented so as to permit application of a magnetic field having a substantially uniform polarity to a user. The magnets may also be positioned on the array so that adjacent magnets have opposite polarities.

Other objects, advantages and applications of the present invention will be made clear by the following detailed description of a preferred embodiment of the invention. The description makes reference to drawings in which:

BRIEF DESCRIPTION OF THE DRAWINGS

FIG. 10 is a view of the prior art;

FIG. 11 is a side view of an alternate embodiment of the present invention;

FIG. 12 is another alternate embodiment of the present invention; and

FIG. 13 is another alternate embodiment of the present invention.

DETAILED DESCRIPTION

Figure 1A:
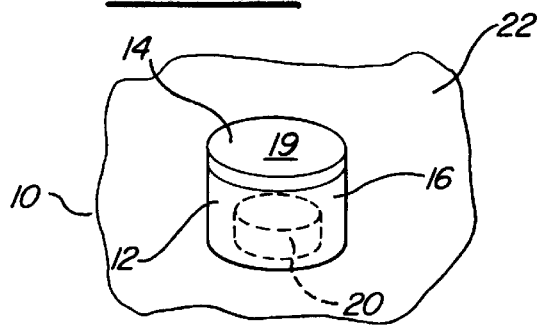
FIG. 1A is a partial perspective view of the preferred embodiment of the invention.

The preferred embodiment of the invention, as depicted in FIG. 1, includes a housing 12 which is constructed of a non-magnetic material. Non-magnetic housing 12 includes separable portions 14 and 16 which mate so as to form an internal cavity 18. Non-magnetic housing 12 also has an exterior surface 19 which is attached to cloth 22 by adhesive, tensioning wrap, velcro or other similar means. Alternately, the exterior surface 19 of housing 12 may be removably attached to the skin or hide of an individual by a removable adhesive, such as commercially available two-sided tape, glue or other tacky substance.

Magnet 20 is placed within internal cavity 18, magnet 20 being configured to be smaller than internal cavity 18 so that it is freely movable within internal cavity 18. Thus, movement of the non-magnetic housing 12, cloth 22 and the user results in movement of the magnet within the internal cavity and relative movement between the user and magnet 20, subjecting the user to a moving magnetic field which is known to have therapeutic benefits.

Figure 2:
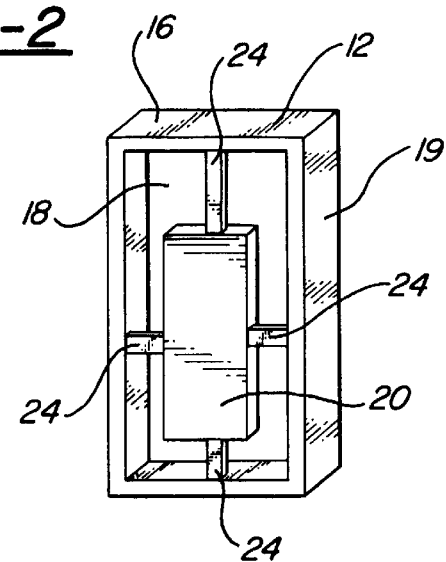
FIG. 2 is a perspective view of an alternate embodiment having the magnet suspended within a housing.

Magnet 20 may be suspended in housing 12 by flexible or other means, such as springs or the elastic bands 24 shown in FIG. 2. Magnet 20 may be suspended pivotally from a rigid member, the pivoting action of the rigid member with respect to the housing permits movement of magnet 20 relative to the user. Preferably, elastic bands 24 are used to suspend magnet 20 in both the vertical and horizontal direction, although alternate embodiments may utilize springs to suspend the magnet in either a horizontal or a vertical direction. The elasticity in the springs or elastic bands enables magnet 20 to respond to all movements of housing 12 and the user, and permits magnet 20 to move freely within housing 12. Housing 12 may be constructed in a variety of shapes, including cylindrical, square, rectangular or other geometric shape. Magnets 20 contained within housings 12 may also be of a variety of shapes, and need not be of the same shape as its housing.

The housing may be configured so as to restrict, in one or more directions, the movement of the magnet within the housing, thereby enabling selection of the polarity of the magnetic field to which the user is subjected. For example, a disk-shaped magnet may be placed within a housing having a height which prevents the magnet from flipping over within the housing, or a rectangular magnet may be placed within a housing so that one face of the magnet is always pointing toward the subject tissue. Thus, the present invention may subject a user to a dynamic magnetic field having a preferred polarity.

Figure 1B:
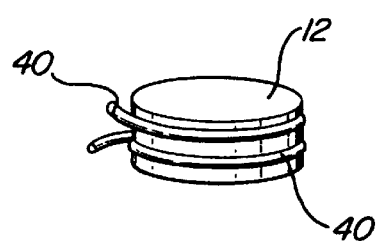
FIG. 1B is an alternate embodiment of the present invention.

Alternately, different mechanisms may be utilized to move magnets 20 placed within housing 12, such as by providing an orifice in the housing so that a stream of fluid such as a gas or liquid may be forced into the housing, the stream of fluid being sufficiently strong so as to move the magnet, thus creating relative movement between the magnet and the housing. If permanent magnets are utilized, an electrically conductive wire 40, as shown in FIG. 1B, may be wrapped around housing 12 or placed near magnet 20 so that, as current passes through the wire, the magnet is caused to move relative to the user and/or the housing. Additionally, mechanical devices including cams, gears and/or linkages may be utilized to move the magnets. These mechanical devices may be powered through motorized means or may be connected to devices moving in the surrounding environment which will cause the mechanical device to move the magnet. An external exciter magnet may be positioned near the magnet of the present invention, the external exciter magnet generating a sufficiently strong magnetic field to cause movement of the magnet contained within the housing or positioned near the area to be treated.

Preferably, housings 20 are manufactured from a non-electrically conductive plastic, such as polyester or polyethylene, and have sufficient rigidity so as to retain their overall shape. Depending upon the application, housing 12 may be of a substance which does not interfere with and is not toxic to plant, animal or human tissue, so as to enable housing 12 to be embedded or inserted within the area of tissue of the user to be treated.

Figure 3:
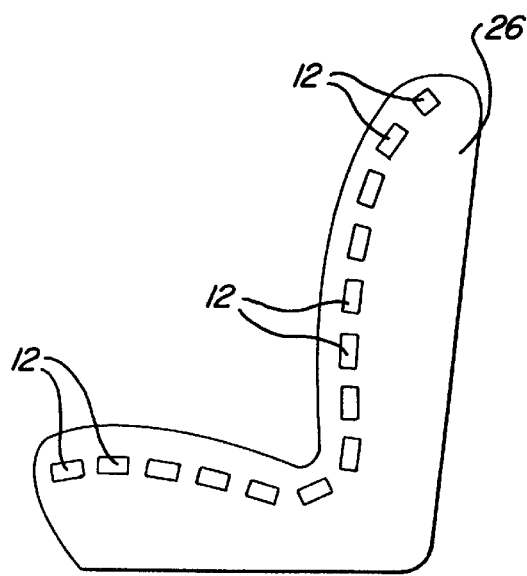
FIG. 3 is a view of an alternate embodiment of the invention whereby a plurality of the housings depicted in FIG. 1A are contained within a seat.

As depicted in FIG. 3, housings 12 may be embedded in seat 26 suitable for supporting the user. Seat 26 is preferably located in a moving vehicle, so that movement of the vehicle and the seat causes enhanced movement of magnet 20 positioned within housings 12, thereby subjecting the user positioned in seat 26 to a moving magnetic field. In alternate embodiments, housing 12 may be positioned within other moving structures which are used to support individuals, such as stretchers or the like. Additionally, housings may be contained within handles of golf clubs, bats, racquets, bicycle handlebar grips and the like. Also, housings may be embedded in shoes such as athletic shoes and braces such as knee, ankle and wrist braces or other supports.

Figure 4:
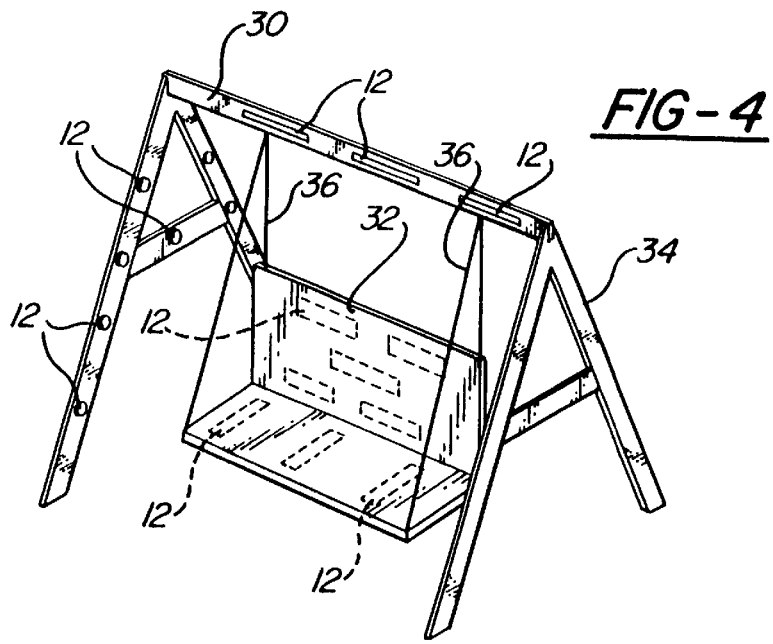
FIG. 4 is a perspective view of an alternate embodiment of the invention whereby the housings are positioned on a swing.

As depicted in FIG. 4, housings 12 may be mounted to a swing 30 having a seat 32 and a support 34, seat 32 being suspended by cables 36 from support 34. Housings 12 may be mounted to a support 34 or seat 32, whereby the movement of swing seat 32 causes movement of magnets 20 within housings 12 so as to subject the user in swing 30 to a variable magnetic field.

Figure 5:
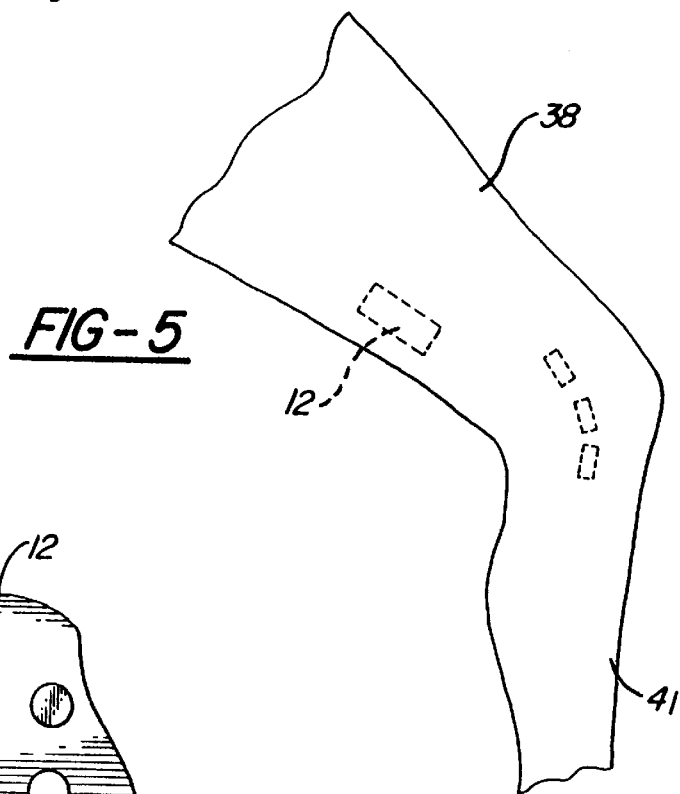
FIG. 5 is a view of an alternate embodiment of the invention whereby the housing is embedded within an individual.

Alternatively, housing 12 may be embedded within the muscle area 38 of leg 40 of an individual to be treated. FIG. 5 depicts a housing 12 embedded within the musculature of leg 40, so that the tissue surrounding the housing 12 is subjected to a moving magnetic field whenever the individual moves.

Alternate embodiments of the invention include suspension of the magnet from a frame 42, depicted in FIG. 13, so that magnet 20 will move proximate to the area to be treated. The magnet may be suspended by elastic bands 24 or pivotable member 44 from frame 42, in a manner similar to the suspension of the magnet within housing 12. While containing magnet 20 within a housing is preferable in certain applications, it is not required in all applications of the moving magnetic fields of the present invention.

If a particular polarity of the magnetic field is preferred, magnet 20 may be affixed to pivotable member 44 so that the appropriate polarity is applied to the user.

While permanent magnets of any strength may be utilized in the present invention, magnets having strengths within the range of 500 to 2000 Gauss are preferred. The permanent magnets are preferably rare earth magnets such as neodymium iron boron or samarium cobalt magnets, although other permanent magnets may be utilized. Alternately, electromagnets may be utilized in the present invention, and in embodiments where magnet 20 is suspended utilizing an elastic member or pivotable member, electromagnets may be easily utilized by utilizing the elastic bands to suspend the electromagnet within the housing. Current may be supplied to the electromagnet by wires penetrating through the housing and connecting to an external power source.

Figure 6:
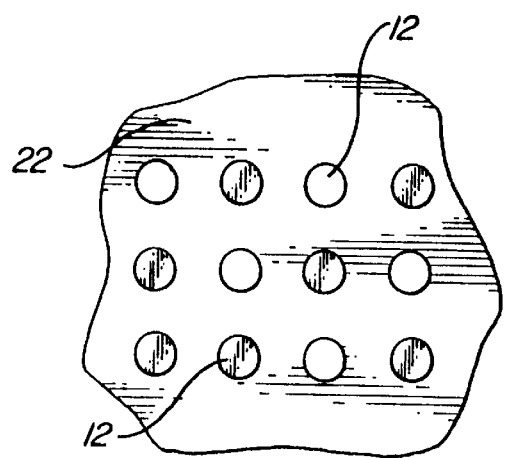
FIG. 6 is a view of another alternate embodiment of the invention.

FIG. 6 depicts an array of permanent magnets enclosed in housings 12 which may be affixed to the user or to a moving object within the user's environment such as a vehicle seat. Preferably, the magnets in an array are spaced far enough apart so that they will not interact with each other and prevent movement of magnets 20. The area between the magnets will be filled with return path magnetic flux which will measure as opposite polarity on a Hall effect Gauss meter.

Figure 7:
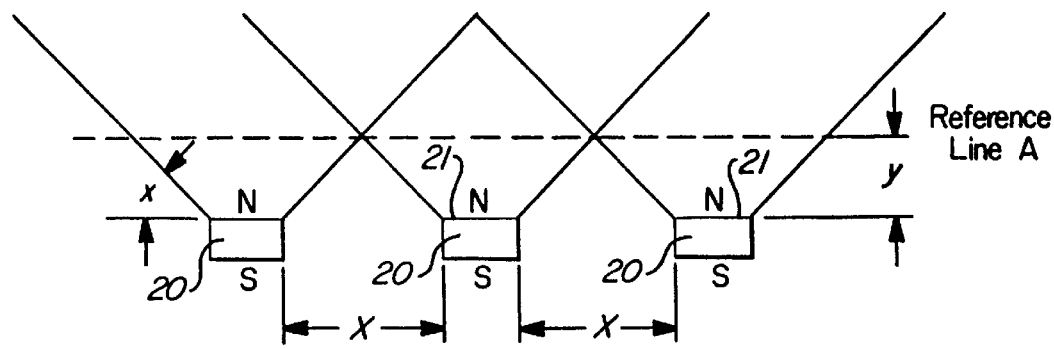
FIG. 7 is a side view of an alternate embodiment of the present invention.

If uniform north or south pole orientation is desired, the distance between the magnets in the array should position the target tissue within the intersecting cones of preferred pole flux as depicted in FIG. 7. Thus, if the cone angle Z for a given magnet is 45°, the distance X between magnets 20 must be twice the distance Y from the magnet face 21 to the subject tissue positioned at reference line A to maintain a single polar environment. Thus, in FIG. 7, if X equals two inches, Y equals one inch.

If there is relative movement between the subject tissue and the array caused by movement of the either the array of magnets or the subject, a moving magnetic field of like polarity will result. If the spacing between the magnets is wider or if the subject tissue is closer to the magnetic array so that portions of the subject tissue are not within the cone of preferred pole flux, then the subject tissue will not be constantly in a single pole environment since the space between magnets contains the return path flux which is of the opposite pole. This configuration is also effective because it provides greater variation in flux density and superior eddy current generation effects in tissue moved relative to the array.

Figure 8:
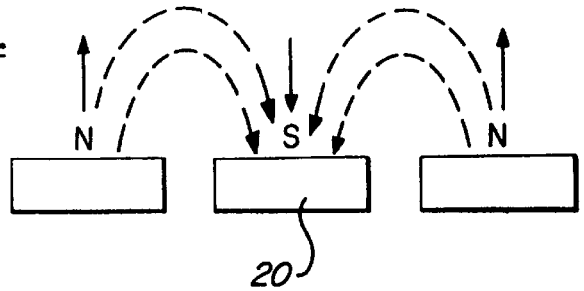
FIG. 8 is a view of the prior art.

FIG. 8 depicts the flux from the outermost north zones passing through the central south zone on their return path. Since their direction is now reversed in the return path, this flux reinforces the south pole zone and amplifies the intensity of the field in the central area of magnet 20. FIG. 10 also shows the return flux patterns of a magnet, with divergent flux within the north side of the cone-shaped area 50, and convergent flux inside the cone-shaped area 52.

Figure 9:
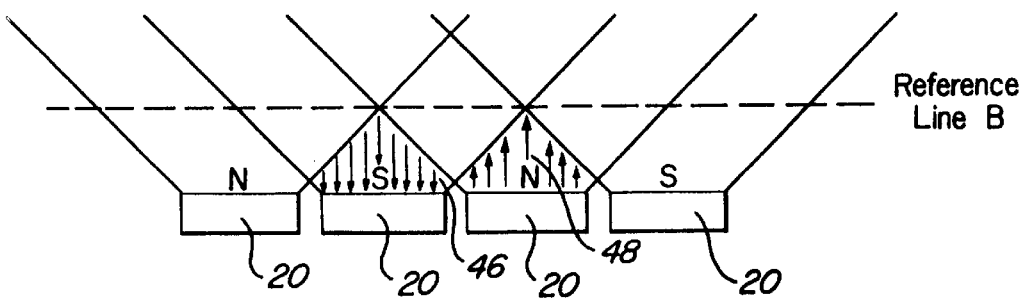
FIG. 9 is a side view of an alternate embodiment of the invention.

If magnets are positioned in close proximity to each other, as depicted in FIG. 9, there will be alternating zones of convergent and divergent flux (north and south) which will be strongest in the areas designated as 46 and 48. Thus, an array may be created with alternating pole elements which are closely spaced to create alternating convergent and divergent field exposure due to relative movement of the subject tissue and the array. By varying the width of the magnetic elements in FIG. 9, the height of the reinforced strong zone (below Reference Line B) can be increased, thereby increasing the reach of the multipolar array. If the array is moved on a parallel plane relative to the subject tissue, a more powerful field is generated with the depth of penetration determined by the pole width.

Axially rotating magnets do not produce magnetic fields which are as effective as non-rotating, moving magnets because, as the magnet rotates on its axis, the north and south poles, which are considered to be the treatment medium, are only oriented directly at the target tissue for a brief portion of the rotation of the magnet. For at least half the time of rotation, the magnet is parallel to the tissue with the magnetically intense zone aimed away from the tissue. In moving magnets of the type disclosed herein, the magnetically intense zone may be aimed at the tissue at all times, despite movement of the magnet. Thus, higher flux density may be applied to the tissue while maintaining the polarity of the magnetic field aimed at the tissue to be treated.

Another alternate embodiment, depicted in FIG. 11, includes a handle 54 having an end 55 which is attached to a flexible member 56. A magnet 20, preferably a permanent ceramic ferrite or neodymium magnet, is positioned proximate to end 60 of flexible member 56, which is sufficiently long and flexible so that, upon movement of handle 54, magnet 20 oscillates in an accentuated fashion. The user may oscillate magnet 20 over afflicted areas. Alternatively, handle 54 and flexible member 56 may be constructed as a single member such as of plastic. Additionally, a housing 12 may be affixed to end 60 of flexible member 56 so as to provide even greater movement of magnet 20 with respect to the user.

Still another alternate embodiment of the present invention includes magnets 20 positioned on a rigid substrate 62 such as a planar wooden board, a plastic plank or the like. The array, depicted in FIG. 12, may be moved relative to the user so that the magnets remain a fixed distance from the user, e.g., substantially parallel to the tissue to be treated. Magnets 20 within the array may be positioned so that adjacent magnets have opposite polarities, or all magnets may be positioned in a manner such that all magnets have the same polarity. The magnets may be located on the substrate 62 so as to maximize the magnetic flux at a predetermined distance from the substrate 62.

I claim:

1. A therapeutic device adapted to subject a user to a magnetic field, the therapeutic device comprising:

a frame;

at least one magnet;

means for suspending the magnet substantially within the frame so that the magnet is movable in a horizontal and/or vertical direction relative to the frame; and means for physically supporting the frame relative to the user such that, as the user moves, the frame moves substantially with the user;

whereby movement of the frame causes movement of the magnet with respect to the frame, resulting in relative movement between the user and the magnet.

2. The therapeutic device of claim 1, wherein the magnet is positioned so that the user is subjected to a magnetic field having a particular orientation.

3. The therapeutic device as claimed in claim 1, wherein the magnet is a permanent magnet.

4. A therapeutic device adapted to subject a user to a magnetic field, the therapeutic device comprising:

a frame;

at least one magnet;

means for suspending the magnet within the frame so that the magnet is movable in a horizontal and/or vertical direction relative to the frame;

an object positioned proximate to the user, the object moving with respect to the user;

means for attaching the frame to the object so that, as the object moves, the frame moves substantially with the object;

whereby movement of the frame and the object causes movement of the magnet with respect to the frame and the user.

5. The therapeutic device as claimed in claim 4, wherein the means for suspending the magnet within the frame comprises at least one elastic band.

6. The therapeutic device as claimed in claim 4, wherein the means for suspending the magnet within the frame comprises at least one spring.

7. The therapeutic device as claimed in claim 4, wherein the means for suspending the magnet within the frame comprises a pivotable linking member.

8. The therapeutic device as claimed in claim 4, wherein the object is a seat in a vehicle.

9. A therapeutic device adapted to subject a user to a magnetic field, the therapeutic device comprising:

at least one non-magnetic housing, each housing having an internal cavity;

means for physically supporting each housing relative to the user such that, as the user moves, the housing moves substantially with the user; and at least one magnet disposed within the internal cavity of each non-magnetic housing, the magnet being smaller that the internal cavity so as to be freely moveable within the internal cavity;

whereby movement of the non-magnetic housing causes movement of the magnet within the internal cavity resulting in relative movement between the user and the magnet.

10. The therapeutic device as claimed in claim 9, wherein the means for positioning the non-magnetic housing proximate to the user includes means adapted to attach the housing to the user.

11. The therapeutic device as claimed in claim 10, wherein the means for attaching comprises adhesive.

12. The therapeutic device as claimed in claim 9, further including means for suspending the magnet within the internal cavity of the housing so that the magnet is freely moveable within the internal cavity.

13. The therapeutic device as claimed in claim 12, wherein the means for suspending the magnet within the internal cavity of the housing is an elastic band.

14. The therapeutic device as claimed in claim 12, wherein the means for suspending the magnet within the internal cavity of the housing comprises at least one spring.

15. The therapeutic device as claimed in claim 9, wherein the magnet is a permanent magnet.

16. The therapeutic device as claimed in claim 9, wherein the means for positioning the non-magnetic housing proximate to the user comprises a shoe.

17. The therapeutic device as claimed in claim 9, further including means for magnetically exciting the magnet disposed within the housing so that the magnets are caused to move relative to the housing.

18. The therapeutic device as claimed to claim 17, wherein the means for magnetically exciting the magnet includes an electrically conductive wire coiled about the housing.

19. A therapeutic device adapted to a magnetic field to a user, the therapeutic device comprising:

a non-magnetic housing having an internal cavity;

means for embedding the non-magnetic housing within the user; and at least one magnet disposed within the internal cavity of the non-magnetic housing, the magnet being smaller that the internal cavity of the non-magnetic housing so as to be freely moveable within the internal cavity;

whereby movement of the non-magnetic housing and the user causes movement of the magnet within the internal cavity resulting in relative movement between the user and the magnet.

20. A therapeutic device comprising:

a handle having an end graspable by a user;

a magnet;

a flexible member disposed between the end of the handle and the magnet so that, as the handle is moved, the flexible member causes the magnet to oscillate in an accentuated motion.

21. A therapeutic device for subjecting a user's tissue to a moving magnetic field, the device comprising:

a substantially planar member;

a plurality of magnets affixed to the substantially planar member; and means for moving the substantially planar member along a plane substantially parallel to the tissue being treated.

22. The therapeutic device of claim 21 wherein the magnets are spaced so as to subject a user to a magnetic field having a single polar orientation.

23. The therapeutic device of claim 21 wherein the magnets are affixed to the substantially planar member so that magnets having opposite polar orientations are positioned proximate to one another.

* * * * *